United States Patent [19]

Ponpipom et al.

[11] Patent Number: 5,684,152
[45] Date of Patent: Nov. 4, 1997

[54] PREPARATION OF CARBOXYALKYL DERIVATIVES AS INHIBITORS OF MATRIX METALLOPROTEINASES

[75] Inventors: Mitree M. Ponpipom, Branchburg; William K. Hagmann, Westfield, both of N.J.

[73] Assignee: Merck & Co., Inc., Rahway, N.J.

[21] Appl. No.: 716,042

[22] Filed: Sep. 19, 1996

Related U.S. Application Data

[60] Provisional application No. 60/005,272, Sep. 28, 1995.

[51] Int. Cl.[6] .................. C07C 39/225; C07D 209/02; C07D 207/00; C07D 263/04; C07D 277/04; C07D 307/00; C07D 413/08; C07D 279/00

[52] U.S. Cl. .................. 544/242; 544/264; 544/336; 544/358; 546/152; 546/193; 546/249; 548/152; 548/206; 548/213; 548/215; 548/221; 548/335.1; 548/343.5; 548/250; 548/440; 548/469; 548/470; 548/489; 548/491; 548/530; 549/6; 549/23; 549/30; 549/33; 549/49; 549/229; 549/266; 549/273; 549/307; 549/313; 568/735

[58] Field of Search .................. 544/242, 336, 544/358, 264; 546/152, 193, 249; 548/152, 206, 213, 335.1, 343.5, 250, 215, 221, 440, 469, 470, 489, 491, 530; 549/6, 23, 30, 33, 49, 229, 313, 266, 273, 307; 568/735

[56] References Cited

FOREIGN PATENT DOCUMENTS 274234  7/1988  European Pat. Off. .
94/12169  6/1994  WIPO .

OTHER PUBLICATIONS

G.M. Mc Geehan et al., Nature; 370 p. 558 (1994).
A.J.H. Gearihg et al., Nature 370; p. 555 (1994).
K.M. Mohler et al., Nature; 370, pp. 218 (1994).
K.A. Hasty et al. Arthur. Rheum; 33, pp. 388–397 (1990).
A. Blanckaert et al., Clin. Chem Acta; 185, pp. 73–80 (1989).
A. Ito et al., Arch Biochem Biophys; 267, pp. 211–216 (1988).
G. Murphy et al., Biochem. J.; 248, pp. 265–268 (1987).
Y. Ogata et al., J. Biol. Chem.; 267, pp. 3581–3584 (1992).
L.M. Matrisian et al., Proc. Nat'l., Acad. Sci., USA 83, pp. 9413–9417 (1986).
S.M. Wilhelm et al., Ibid; 84, pp. 6725–6729 (1987).
Z. Werb et al. J. Cell Biol.; 109, pp. 872–879 (1989).
L.A. Liotta et al.; 49, pp. 636–649 (1983).
V.J. Uitto et al. J. Periodontal Res.; 16, pp. 417–424 (1981).
W.H. Baricos, Biochem. J.; 254, pp. 609–612 (1988).
A. M. Henney et al., Proc. Nat'l Acad. Sci USA; 88, pp. 8154–8158 (1991).
P.G. Winyard et al. FEBS Letts: 279 (1), pp. 91–94 (1991).

*Primary Examiner*—Johann Richter
*Assistant Examiner*—Jane C. Oswecki
*Attorney, Agent, or Firm*—Sylvia A. Ayler; Mark R. Daniel

[57] ABSTRACT

Carboxy-peptidyl compounds of Formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, coronary thrombosis associated with atherosclerotic plaque rupture, and aneurysmal aortic disease. This invention relates to a process of making the carboxy-peptidyl compounds of formula I.

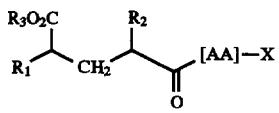

10 Claims, No Drawings

PREPARATION OF CARBOXYALKYL DERIVATIVES AS INHIBITORS OF MATRIX METALLOPROTEINASES

This application claims the benefit of Provisional Application No. 60/005272 filed Sep. 28, 1995.

BACKGROUND OF THE INVENTION

The development of new methods for the preparation of carboxyalkyl derivatives is of continuing importance, since these compounds have interesting biological activity and are useful as inhibitors of matrix metalloendoproteinase and in the treatment of matrix metalloendoproteinase-mediated diseases.

Stromelysin (aka. proteoglycanase, matrix metalloproteinase-3 (MMP-3), procollagenase activator, "transin"), collagenase (aka. interstitial collagenase, matrix metalloproteinase-1 (MMP-1)), and gelatinase (aka. type IV collagenase, matrix metalloproteinase-2 (MMP-2), 72 kDa-gelatinase or type V collagenase, matrix metalloproteinase-9, (MMP-9), 92 kDa-gelatinase) are metalloendoproteinases secreted by fibroblasts and chondrocytes, and are capable of degrading the major connective tissue components of articular cartilage or basement membranes. See G. M. McGeehan et al., Nature 370, 558 (94); A. J. H Gearihg et al., Nature 370, p555 (94); K. M. Mohler et al., Nature 370, p218 (94) and EP274,234. Elevated levels of both enzymes have been detected in joints of arthritic humans and animals: K. A. Hasty, R. A. Reife, A. H. Kang, J. M. Stuart, "The role of stromelysin in the cartilage destruction that accompanies inflammatory arthritis", *Arthr. Rheum.*, 33, 388–97 (1990); S. M. Krane, E. P. Amento, M. B. Goldring, S. R. Goldring, and M. L. Stephenson, "Modulation of matrix synthesis and degradation in joint inflammation", *The Control of Tissue Damage*, A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthritic cartilage", *Clin. Chim. Acta*, 185 73–80 (1989). Each enzyme is secreted from these cells as an inactive proenzyme which is subsequently activated. There is evidence that stromelysin may be the in vivo activator for collagenase, implying a cascade for degradative enzyme activity: A. Ho, H. Nagase, "Evidence that human rheumatoid synovial matrix metalloproteinase 3 is an endogenous activator of procollagenase", *Arch Biochem Biophys.*, 267, 211–16 (1988); G. Murphy, M. I. Crockett, P. E. Stephens, B. J. Smith, A. J. P. Docherty, "Stromelysin is an activator of procollagenase", *Biochem. J.*, 248, 265–8 (1987); Y. Ogata, J. J. Engh. ld, H. Nagase, "Matrix metalloprotease-3 (stromelysin) activates the precusor for human matrix metalloproteinase-9," *J. Biol. Chem.* 267, 3581–84 (1992). Inhibiting stromelysin could limit the activation of collagenase and gelatinase as well as prevent the degradation of proteoglycan.

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD's), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

There is extensive literature on the involvement of these metalloproteinases in arthritis. That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, *J. Orthopaedic Res.*, 6, 103–8 (1988).

Stromelysin and collagenase inhibitors are also believed to have utility in preventing articular cartilage damage associated with septic arthritis, controlling tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", *Proc. Natl. Acad. Sci., USA*, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", *Ibid.*, 84, 6725–29 (1987); Z. Werb et al., "Signal transduction through the fibronectin receptor induces collagenase and stromelysin gene expression", *J. Cell Biol.*, 109, 872–889 (1989); L. A. Liotta, C. N. Rao, S. H. Barsky, "Tumor invasion and the extracellular matrix", *Lab. Invest.*, 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant tumor cells", in *Metastasis: Ciba Foundation Symposium*; Wiley, Chichester, 1988, pp. 193–210; controlling periodontal diseases, such as gingivitis, V. J. Uitto, R. Applegren, P. J. Robinson, "Collagenase and neutral metalloproteinase activity in extracts of inflammed human gingiva", *J. Periodontal Res.*, 16, 417–424(1981); degrading structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", *Biochem. J.*, 254, 609–612 (1988); preventing the rupture of atherosclerotic plaques leading to coronary thrombosis, A. M. Henney, P. R. Wakeley, M. J. Davies, K. Foster, R. Hembry, G. Murphy, S. Humphries, "Localization of stromelysin gene expression in atherosclerotic plaques by in situ hybridization", *Proc. Nat'l. Acad. Sci. USA*, 88, 8154–8158 (1991); preventing or delaying the degradation of the connective tissue matrix that stabilizes the atherosclerotic plaques, thereby preventing events leading to acute coronary thrombosis; treating degenerative aortic disease associated with thinning of the medial aortic wall; and degrading other in vivo substrates including the inhibitors $\alpha_1$-proteinase inhibitor and may therefore influence the activities of other proteinases such as elastase: P. G. Winyard, Z. Zhang, K. Chidwick, D. R. Blake, R. W. Carrell, G. Murphy, "Proteolytic inactivation of human $\alpha_1$-antitrypsin by human stromelysin", *FEBS Letts.*, 279, 1, 91–94 (1991).

An approach to the synthesis of carboxyalkyl derivatives is disclosed in PCT WO 94/12169 and is depicted in Scheme 1 as follows:

SCHEME 1

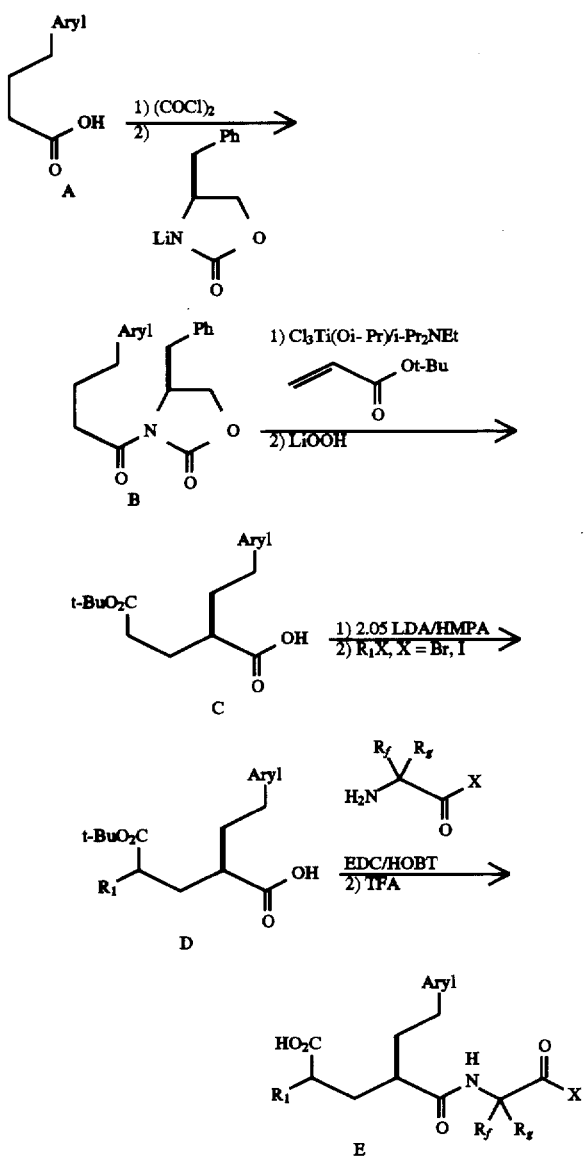

Throughout the instant application, the following abbreviations are used with the following meanings:

| | |
|---|---|
| DMPU | 1,3-dimethyl-3,4,5,6-tetrahydro-2[1H]-pyrimidinone |
| EDC | 1-(3-dimethylaminopropyl)-3-ethylcarbodi-imide |
| Et | ethyl |
| eq. | equivalent(s) |
| h. | hour |
| Oi | oxy-isopropyl |
| HOBT,HOBt | Hydroxybenztriazole |
| HPLC | High pressure liquid chromatography |
| HMPA | Hexamethyl Phosphoramide |
| LDA | Lithium diisoproylamide |
| Me | methyl |
| MeOH | methanol |
| NIS | N-iodosuccinimide |
| NMM | N-Methylmorpholine |
| NMR | Nuclear Magnetic Resonance |
| Ph | phenyl |
| Pr | propyl |

| | |
|---|---|
| prep. | prepared |
| PTS | para-toluene sulfonic acid |
| rt | room temperature |
| TFA | Trifluoroacetic acid |
| THF | Tetrahydrofuran |
| TLC | Thin layer chromatography |

The inhibitors described in Scheme I are prepared as follows. An arylalkyl carboxylic acid is first converted to its corresponding acid chloride using oxallyl chloride and this is used to acylate lithio-4-benzyl-2-oxazolidinone. The derived imide is then enolized with $Cl_3Ti(Oi-Pr)$ in the presence of Hunig's base and alkylated with t-butyl acrylate. The chiral auxilliary is then remove with lithium hydroperoxide and the resulting acid ester enolized with lithium diisoprpyl amide and alkylated with an alkyl halide. The acid is then coupled to an amine and the t-butyl ester deprotected with trifluoroacetic acid to afford the desired inhibitors. However, this approach involves an alkylation step that results in an approximately 3:1 mixture of products, which then has to be separated by column chromatography via their esters.

SUMMARY OF THE INVENTION

This invention is concerned with a novel process for the preparation of carboxyalkyl derivatives of Formula I (wherein $R_1$, $R_2$, $R_3$, AA and X are described below) which are useful inhibitors of matrix metalloendoproteinase-mediated diseases including degenerative diseases (such as defined above) and certain cancers.

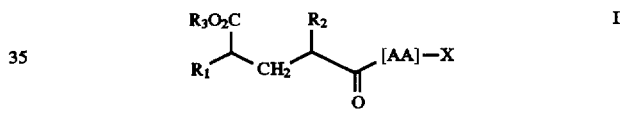

The instant process offers selectivity in the alkylation step by not producing isomeric products that require column chromatography for separation.

DETAILED DESCRIPTION OF THE INVENTION

The instant invention encompasses the process of making a compound of Formula I

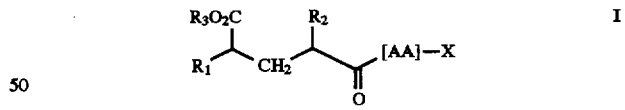

or a pharmaceutically acceptable salt thereof wherein:

$R_1$ is hydrogen, mono or disubstituted $C_{1-8}$alkyl, $C_{1-6}$alkoxy or substituted $C_{2-8}$ alkenyl wherein the substituents are independently selected from the group consisting of:

(a) hydrogen, (b) carboxy, (c) aminocarbonyl, (d) $C_{1-6}$alkoxy, (e) $C_{1-6}$alkylcarbonyl, (f) Aryl wherein the Aryl group is selected from the group consisting of (1) phenyl, (2) naphthyl, (3) pyridyl, (4) furyl, (5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(g) aryloxy wherein the aryl groups are defined above;

(h) aroyl wherein the aryl groups are defined above;

(i)

wherein $R_a$ and $R_b$ are each independently hydrogen; Aryl or heteroaryl and mono and di-substituted aryl or heteroaryl as defined above; or substituted $C_{1-6}$alkyl wherein the substitutent is selected from hydroxy, halo, and aryl or heteroaryl, or wherein $R_a$ and $R_b$ are joined such that together with the nitrogen and carbon atoms to which they are attached, there is formed a saturated or unsaturated lactam or benzolactam ring such as

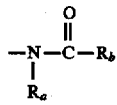

wherein n is 1, 2 or 3 or benzo fused lactam ring such as

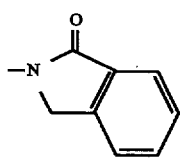

wherein the lactam portion thereof is a ring of 5, 6, 7 or 8 atoms, said lactam or benzolactam to have a single hetero atom;

(j)

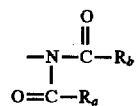

wherein $R_a$ and $R_b$ are each independently hydrogen; aryl or heteroaryl and mono and di-substituted aryl or heteroaryl as defined above; or substituted $C_{1-6}$alkyl wherein the substitutent is selected from hydroxy, halo, and aryl, or wherein $R_a$ and $R_b$ are joined such that together with the nitrogen and carbon atoms to which they are attached, there is formed a saturated or unsaturated lactim (or imide) such as

or benzolactim (or imide) ring such as

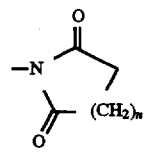

wherein the lactim portion thereof is a ring of 5, 6, 7 or 8 atoms, said lactim or benzolactim to have a single hetero atom;

(k) amino and mono or disubstituted amino wherein the substituent is selected from $C_{1-6}$ alkyl and Aryl where aryl or heteroaryl is defined above;

(l)

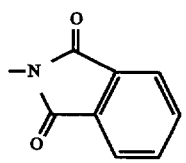

Wherein $R_a$ and $R_b$ are each independently hydrogen; or $C_{1-6}$ Alkyl; aryl as defined above or Aryl$C_{0-6}$Alkyl or mono or di substituted Aryl$C_{0-6}$Alkyl wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined above; or wherein $R_a$ and $R_b$ are joined such that together with the nitrogen and oxygen atoms to which they are attached, there is formed a saturated or unsaturated monocyclic urethane or benzofused cyclic urethane such as

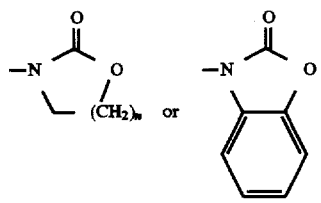

wherein the urethane ring contains 5, 6, 7 or 8 atoms, said ring to contain 2 heteroatoms;

(m)

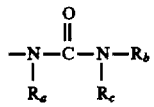

Wherein $R_a$, $R_b$, and $R_c$ are each independently hydrogen; or $C_{1-6}$ Alkyl; or ArylC$_{0-6}$Alkyl or mono or di substituted ArylC$_{0-6}$Alkyl wherein the substitutents are independently selected from $C_{1-6}$alkyl, $C_{1-6}$alkyloxy, halo, hydroxy, amino, $C_{1-6}$alkylamino, aminoC$_{1-6}$alkyl, carboxyl, carboxylC$_{1-6}$alkyl, and $C_{1-6}$alkylcarbonyl and aryl is defined as above; or wherein $R_a$ and $R_b$ are joined such that together with the nitrogen atoms to which they are attached, there is formed a saturated or unsaturated monocyclic urea or benzofused cyclic urea such as

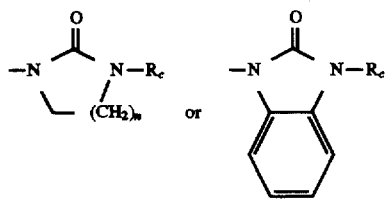

wherein the urea ring contains up to 8 atoms, said ring to contain 2 heteroatoms; or $R_b$ and $R_c$ are joined such that together with the nitrogen atom to which they are attached, there is formed a saturated or unsaturated monocyclic ring or benzofused ring containing 5, 6, 7 or 8 atoms, said ring to contain 1 heteroatom;

(n)

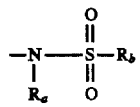

Wherein $R_a$ and $R_b$ are each independently hydrogen; or $C_{1-6}$ Alkyl; or ArylC$_{0-6}$Alkyl or mono or di substituted ArylC$_{0-6}$Alkyl wherein the substitutents are independently selected from $C_{1-6}$alkyl, $C_{1-6}$alkyloxy, halo, hydroxy, amino, $C_{1-6}$alkylamino, aminoC$_{1-6}$alkyl, carboxyl, carboxylC$_{1-6}$alkyl, and $C_{1-6}$alkylcarbonyl and Aryl is defined as above or wherein $R_a$ and $R_b$ are joined such that together with the nitrogen and sulfer atoms to which they are attached, there is formed a saturated or unsaturated monocyclic sulfonaminde or benzofused cyclic sulfonamide such as

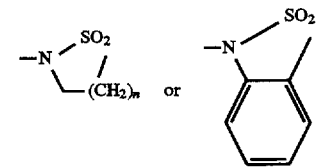

wherein the sulfonamide ring contains 5, 6, 7 or 8 atoms, said ring to contain 2 heteroatoms;

(o)

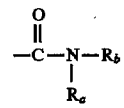

Wherein $R_a$ and $R_b$ are each independently hydrogen; or $C_{1-6}$ Alkyl; or ArylC$_{0-6}$Alkyl or mono or di substituted ArylC$_{0-6}$Alkyl wherein the substitutents are independently selected from $C_{1-6}$alkyl, $C_{1-6}$alkyloxy, halo, hydroxy, amino, $C_{1-6}$alkylamino, aminoC$_{1-6}$alkyl, carboxyl, carboxylC$_{1-6}$alkyl, and $C_{1-6}$alkylcarbonyl and Aryl is defined as above; or $R_a$ and $R_b$ are joined such that together with the nitrogen atom to which they are attached, there is formed a saturated or unsaturated monocyclic ring or benzofused ring containing 5, 6, 7 or 8 atoms, said ring to contain 1 heteroatom;

(p)

Wherein $R_a$ and $R_b$ are each independently hydrogen; or $C_{1-6}$ Alkyl; or ArylC$_{0-6}$Alkyl or mono or di substituted ArylC$_{0-6}$Alkyl wherein the substitutents are independently selected frown $C_{1-6}$alkyl, $C_{1-6}$alkyloxy, halo, hydroxy, amino, $C_{1-6}$alkylamino, aminoC$_{1-6}$alkyl, carboxyl, carboxylC$_{1-6}$alkyl, and $C_{1-6}$alkylcarbonyl and Aryl is defined as above; or $R_a$ and $R_b$ are joined such that together with the nitrogen atom to which they are attached, there is formed a saturated or unsaturated monocyclic ring or benzofused ring containing up to 8 atoms, said ring to contain 1 heteroatom;

$R_2$ is $C_{1-12}$ alkyl, arylC$_{1-4}$alkyl, aryl substituted $C_{1-4}$alkyl, (arylC$_{1-4}$alkyl)-arylC$_{1-4}$alkyl, or biarylC$_{1-4}$alkyl wherein the substituent is $C_{1-3}$alkyl or hydroxy, and wherein the aryl group is selected from the group consisting of:

(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,

(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is
(a) H,
(b) Z, where Z is a pharmaceutically counterion, such as sodium, potassium, calcium or magnesium,
(c) $C_{1-10}$alkyl,
(d) Aryl or Aryl $C_{1-3}$alkyl, wherein the aryl group is selected from the group consisting of
 (1) phenyl, and
 (2) substituted phenyl, wherein the substitutent is carboxy, carboxy$C_{1-3}$alkyl, aminocarbonyl, $C_{1-6}$alkylamino carbonyl;

AA is a single bond or an amino acid of formula II

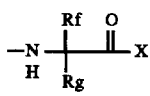

wherein $R_f$ and $R_g$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$ alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substitutent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$ alkyl, or $C_{1-4}$alkyloxy,
(m) substituted pyridyl $C_{1-6}$alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy,
(o) substituted pyimidinyl $C_{1-6}$alkyl wherein the substitutent is hydrogen, hydroxy, carboxy, $C_{1-4}$ alkyl, or $C_{1-4}$alkyloxy, X is

wherein $R_5$ and $R_6$ are each individually selected from the group consisting of:

(a) H,
(b) $C_{1-10}$alkyl,
(c) Aryl or Aryl$C_{1-6}$alkyl, wherein the aryl group is selected from the group consisting of
 (1) phenyl,
 (2) naphthyl,
 (3) pyridyl,
 (4) pyrryl,
 (5) furyl,
 (6) thienyl,
 (7) isothiazolyl,
 (8) imidazolyl,
 (9) benzimidazolyl,
 (10) tetrazolyl,
 (11) pyrazinyl,
 (12) pyrimidyl,
 (13) quinolyl,
 (14) isoquinolyl,
 (15) benzofuryl,
 (16) isobenzofuryl,
 (17) benzothienyl,
 (18) pyrazolyl,
 (19) indolyl,
 (20) isoindolyl,
 (21) purinyl,
 (22) carbazolyl,
 (23) isoxazolyl,
 (24) benzthiazolyl,
 (25) benzoxazolyl,
 (26) thiazolyl, and
 (27) oxazolyl.

and mono and di-substituted Aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl comprising adding a compound of formula 9

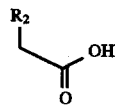

wherein $R_2$ is described as above, and L-prolinol to a solvent, while maintaining a temperature of about 20° C. to about 30° C. to produce a solution containing a compound of structural formula 10

11

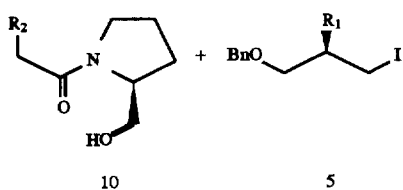

wherein $R_2$ is described above, adding to the solution a strong base in an ether in the presence of DMPU, cooling the solution to from about $-100°$ C. to $-50°$ C., adding a solution of a protected alkyl halide 5, wherein $R_1$ is described above, and warming the solution to from about $-40°$ C. to about $-20°$ C. to produce a solution containing a compound of structural formula 11

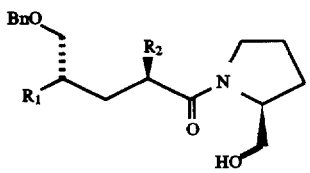

wherein R1, $R_2$ and R' are described above, adding to a solution containing a compound of structural formula 11 in THF-H2O a mineral acid, and heating the solution to from about $50°$ C. to about $100°$ C. to produce a solution containing a compound of structural formula 12

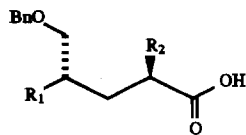

wherein $R_1$, $R_2$ and R' are described above, coupling the compound of structural formula 12 with amino acids, followed by hydrolysis to produce a compound of structural formula 13

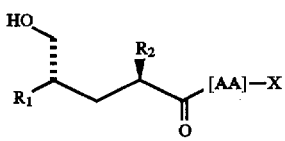

wherein $R_1$, $R_2$, R', AA, and X are described above, oxidizing a compound of structural formula 13 at a temperature of about $-10°$ C. to about $2°$ C. using a Jones reagent to produce a compound of structural formula 14

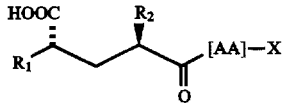

wherein R1, R2 AA, and X are described above and isolating the compound of structural formula 14.

For purposes of this specification, and as appreciated by those of skill in the art, the unsaturated rings such as those described in definitions $R_1$ (d), (e), (g), (h), (i), (j) and (k) are intended to include rings wherein a double bond is present at one, two or more of the available positions. Similarly, the term aryl $C_{0-6}$ alkyl, as found in definitions such as $R_1$ (g), (h), (i), (j) and (k) are intended to describe aryl and aryl $C_{1-6}$ alkyl. Similarly the term (aryl $C_{1-4}$ alkyl-) aryl $C_{1-4}$ arkyl, is intended to describe as aryl $C_{1-4}$ alkyl group wherein the aryl is substituted as aryl $C_{1-4}$ alkyl- such as —$CH_2$ phenyl.

Compounds of the instant invention are conveniently prepared using the procedures described generally below and more explicitly described in the Example section thereafter. The novel process of this invention can be depicted as shown in the following schemes I, and II below:

SCHEME I

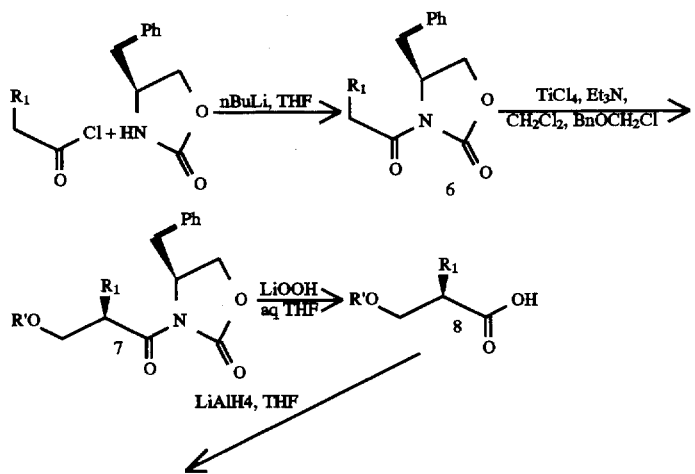

-continued
SCHEME I

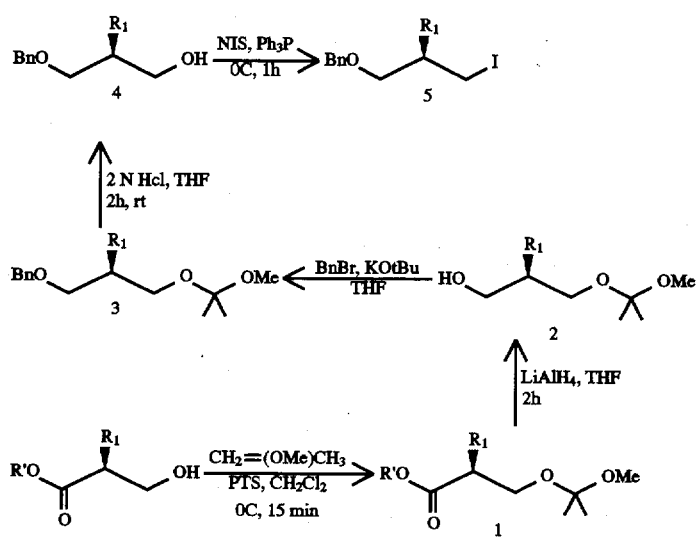

R' = benzyl, Methyl or H
$R_1$ = described herein

SCHEME II

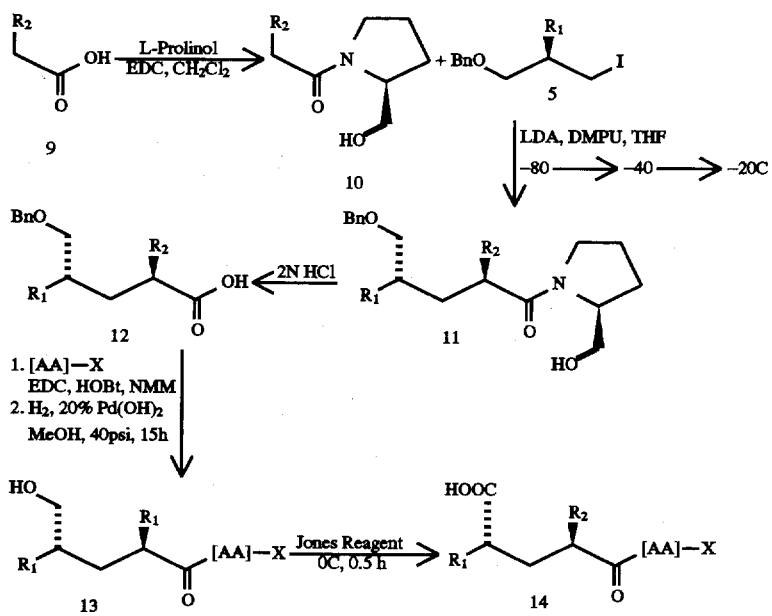

$R_1$, $R_2$, AA, and X are as described herein

Compounds of structural formula 5 are known. See N. Gruenfeld et al., *J. Med. Chem.*, 26, 1277–1282 (1983) and O. Branca and A. Fischli, *Helv. Chim. Acta*, 60, 925–944 (1977).

Preparation of compound 14 comprises adding to a solution containing solvents, belonging to a group consisting of dichloromethane, benzene, toluene, cyclohexane, heptane, EDC, or other carbodiimides, and the like, a carboxylic acid of the formula (9):

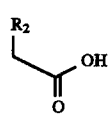

wherein $R_2$ is described as above, and L-prolinol, while maintaining a temperature of about 20° C. to about 30° C. for about 3 to about 36 hours to produce a solution containing a compound of structural formula 10

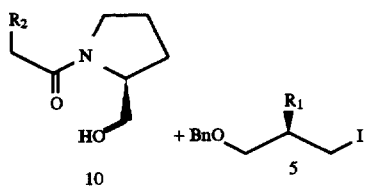

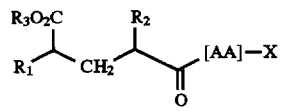

or a pharmaceutically acceptable salt thereof wherein:

$R_1$ is substituted $C_{1-8}$ alkyl;

$R_2$ is $C_{1-12}$ alkyl, aryl$C_{1-4}$alkyl, aryl substituted $C_{1-4}$alkyl, (aryl$C_{1-4}$alkyl) -aryl$C_{1-4}$alkyl, or biaryl$C_{1-4}$alkyl wherein the substituent is $C_{1-3}$alkyl or hydroxy, and wherein the aryl group is selected from the group consisting of:

wherein and $R_2$ is described herein, adding to the solution a strong base such as LDA, LiN(SiMe$_3$)$_2$, KN(SiMe$_3$)$_2$ and the like, in tetrahydrofuran (THF) or other ethers such as ethyl ether, methyl propyl ether and the like, in the presence of DMPU and the like, cooling the solution to from about $-100°$ C. to $-50°$ C., preferrably from about $-90°$ C. to $-75°$ C., adding a solution of a protected alkyl halide 5, wherein $R_1$ is described above, and warming the solution to from about $-40°$ C. to about $-20°$ C. for about 1 to about 30 hours to produce a solution containing a compound of structural formula 11

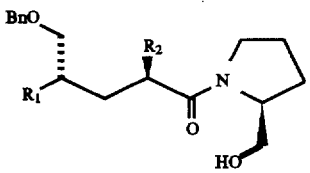

wherein R1, $R_2$ and are described herein, adding to a solution containing a compound of structural formula 11 in THF-H2O mineral acids such as HCl or H2SO4, and the like, wherein the amount of mineral acid in the solution is from about 2 to about 10N, and heating the solution to from about 50° C. to about 100° C. for about 30 minutes to about 24 hours to produce a solution containing a compound of structural formula 12

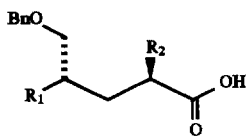

wherein $R_1$, $R_2$ and R' are described herein, coupling the compounds of structural formula 12 with an amino acid followed by hydrolysis to produce a compound of structural formula 13

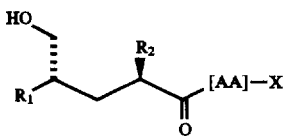

wherein $R_1$, $R_2$, R', AA, and X are described herein, oxidizing a compound of structural formula 13 at a temperature of about $-10°$ C. to about 2° C. using a Jones reagent to produce a compound of structural formula 14

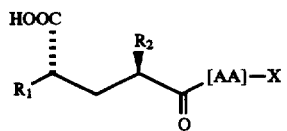

wherein R1, R2 AA, and X are described herein.

A preferred process of the invention encompasses the process of making a compound of formula I (1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents on the aryl group are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is (a) H,
(b) Z, where Z is a pharmaceutically acceptable counterion,
(c) $C_{1-10}$alkyl,
(d) Aryl or Aryl $C_{1-3}$ alkyl, wherein the aryl group is selected from the group consisting of
  (1) phenyl, and
  (2) substituted phenyl, wherein the substitutent is carboxy, carboxy$C_{1-3}$alkyl, aminocarbonyl, $C_{1-6}$alkylaminocarbonyl;

AA is a single bond or an amino acid of formula II

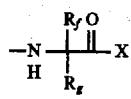
II wherein $R_f$ and $R_g$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substitutent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$ alkyl, or $C_{1-4}$alkyloxy,
(m) substituted pyridyl $C_{1-6}$ alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy,
(o) substituted pyrimidinyl $C_{1-6}$alkyl wherein the substitutent is hydrogen, hydroxy, carboxy, $C_{1-4}$ alkyl, or $C_{1-4}$alkyloxy,
X is

wherein $R_5$ and $R_6$ are each individually selected from the group consisting of:
(a) H,
(b) $C_{1-10}$alkyl,
(c) Aryl or Aryl$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl.

and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl; comprising adding a compound of formula 9

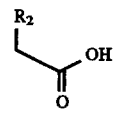

wherein $R_2$ is described as above, and L-prolinol to a solvent belonging to a group consisting of dichloromethane, benzene, toluene, cyclohexane, heptane, and carbodiimides, while maintaining a temperature of about 20° C. to about 30° C. to produce a solution containing a compound of structural formula 10

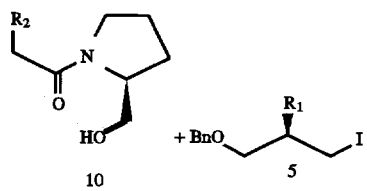

wherein $R_2$ is described above, adding to the solution LDA in tetrahydrofuran in the presence of DMPU, cooling the solution to from about −100° C. to −50° C., adding a solution of a protected alkyl halide 5, wherein $R_1$ is described above, and warming the solution to from about −40° C. to about −20° C. to produce a solution containing a compound of structural formula 11

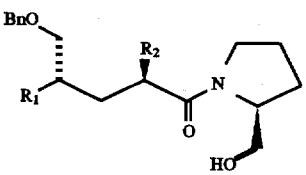

wherein R1, $R_2$ and R' are described above, adding to a solution containing a compound of structural formula 11 in THF-H2O from about 2N to about 10N of a mineral acid belonging to the group consisting of HCl, or $H_2SO_4$ and heating the solution to from about 50° C. to about 100° C. to produce a solution containing a compound of structural formula 12

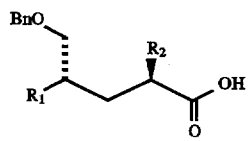

wherein $R_1$, $R_2$ and R' are described above, coupling the compound of structural formula 12 with amino acids, followed by hydrolysis to produce a compound of structural formula 13

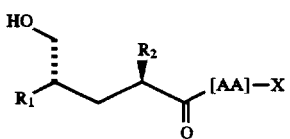

wherein $R_1$, $R_2$, R', AA, and X are described above, oxidizing a compound of structural formula 13 at a temperature of about $-10°$ C. to about $2°$ C. using a Jones reagent to produce a compound of structural formula 14

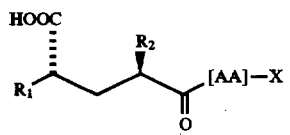

wherein R1, R2 AA, and X are described above and isolating the compound of structural formula 14.

The following Examples are intended to illustrate the preparation of compounds of Formula I, and as such are not intended to limit the invention as set forth in the claims appended, thereto.

EXAMPLE (1)

Methyl 3-(1-Methoxy-1-methyl)ethoxy-2-(S)-methylpropionate

Pyridinium p-toluenesulfonate (2.7 mg, 0.05 mol %) was added to a stirred solution of methyl 3-hydroxy-2-(S)-methylpropionate (2.5 g, 21.2 mmol) and 2-methoxypropene (20 mL, 208 mmol) in dichloromethane (20 mL) at 0° C. After 15 min, the solution was warmed to room temperature in 15 min and quenched with aqueous sodium hydrogencarbonate. The organic layer was separated and washed with brine, dried, and evaporated to a liquid (3.84 g, 95%):

NMR (CDCl$_3$) d 1.18 (d, J=7.0 Hz, CH$_3$CH), 1.32 [s, (CH$_3$)$_2$C], 2.69 (q, CHCH$_3$), 3.18 [s, C(CH$_3$)$_2$OCH$_3$], 3.2 and 3.61 (2 q, CH$_2$O), 3.70 (s, COOCH$_3$).

EXAMPLE (2)

3-(1-Methoxy-1-methyl)ethoxy-2-(R)-methyl-1-propanol

Lithium aluminum hydride (20.2 mL; 1.0M in THF) was added to a stirred solution of (1) (3.84 g, 20.2 mmol) in THF (20 mL) at 0° C. The solution was stirred at room temperature for 2 h and quenched sequentially with water (0.77 mL), 15% NaOH (0.77 mL), and water (2.3 mL). The resulting suspension was filtered, and the filtrate was evaporated to dryness. The residue was partitioned between CH$_2$Cl$_2$ and brine, and the organic layer was separated, dried, and concentrated to a liquid (2.29 g, 70%):

NMR (CDCl$_3$) d 0.89 (d, J=7.0 Hz, CH$_3$CH), 1.36 [s, (CH$_3$)$_2$C], 2.04 (m, OH), 2.76 (q, CHCH$_3$), 3.22 [s, C(CH$_3$)$_2$OCH$_3$], 3.28–3.65 (m, 2 CH$_2$O).

EXAMPLE (3)

Benzyl 3-(1-Methoxy-1-methyl)ethoxy-2-(R)-methyl-1-propyl Ether

Potassium tert-butoxide (1.9 g, 16.9 mmol) was added to a stirred solution of (2) (2.29 g, 14.1 mmol) in THF (30 mL) at 0° C. After 15 min, benzyl bromide (2.01 mL, 16.9 mmol) was added dropwise, and the mixture was stirred at room temperature overnight and partitioned between ethyl ether and water. The organic layer was washed with brine, dried and evaporated to an oil, which was used directly in the next experiment without further purification.

EXAMPLE (4)

Benzyl 3-Hydroxy-2-(S)-methyl-1-propyl Ether

A solution of (3) from above in THF (10 mL) was treated with 2N HCl (30 drops). After 2 h, the solution was evaporated to a residue, which was partitioned between dichloromethane and aqueous sodium hydrogencarbonate. The organic layer was separated and washed with brine, dried, and concentrated to an oil. The crude product was purified by silica gel flash column chromatograpy (hexanes-ethyl acetate, 85:15; v.v) to give (4) (2.07 g, 88% in 2 steps):

NMR (CDCl$_3$) d 0.88 (d, J=7.0 Hz, CH$_3$CH), 2.55 (m, CHCH$_3$), 3.38–3.65 (m, 2 CH$_2$O), 4.53 (s, PhCH$_2$), 7.34–7.36 (m, ArH).

EXAMPLE (5)

Benzyl 3-Iodo-2-(R)-methyl-1-propyl Ether

N-Iodosuccinimide (4.90 g, 21.78 mmol) was added portionwise to a solution of (4) (2.07 g, 12.45 mmol) and triphenylphosphine (5.71 g, 21.77 mmol) in DMF (50 mL) at 0° C. The reaction mixture was stirred at room temperature for 1 h and heated at 40° C. for 5 min. Methanol and n-butanol were added, and the solvents were evaporated in vacuo. The residue was partitioned between ethyl ether and water. The organic layer was washed with sodium bisulfite, brine, dried, and evaporated to dryness. The crude product was purified by silica gel flash column chromatography using hexanes-ethyl acetate (99:1,v/v) as the eluant. Compound (5) was isolated as a liquid (3.63 g, 77%):

NMR (CDCl$_3$) d 0.99 (d, J=6.8 Hz, CH$_3$CH), 1.78 (m, CHCH$_3$), 3.28–3.41 (2 m, 2 CH$_2$O), 4.52 (s, PhCH$_2$), 7.29–7.38 (m, ArH).

EXAMPLE (6)

L-Prolinol 4-(n-Propyl)phenylbutanamide 1-(3-Dimethylaminopropyl)-3-ethylcarbodiimide hydrochloride (EDC; 5.58 g, 29.11 mmol) was added to a solution of 4-(n-propyl)phenylbutanoic acid (5.0 g, 24.24 mmol) and (S)-2-pyrrolidinemethanol (L-prolinol; 2.39 mL, 24.35 mmol) in dichloromethane (30 mL), and the reaction mixture was stirred at room temperature overnight. Dichloromethane was added, and the solution was washed with 5N NaOH, dil HCl, brine, dried, and evaporated to dryness. The crude product was purified by flash column chromatography (CH$_2$Cl$_2$-MeOH, 99:1; v/v) to give (6) (5.26 g, 75%):

NMR (CDCl$_3$) d 0.93 (t, J=7.3 Hz, CH$_3$CH$_2$), 2.30 (t, ArCH$_2$), 2.55 (t, CH$_2$CO), 2.66 (t, CH$_3$CH$_2$), 3.34–3.47 (m, NCH$_2$), 3.53–3.69 (2 m, CH$_2$OH), 4.18–4.25 (m, NCHC), 5.19 (2 d, J=2.2 and 7.8, OH), 7.10 (br s, ArH).

EXAMPLE (7)

L-Prolinol2-(3-Benzyloxy-2-(S)-methylpropyl)-4-(n-Propyl) phenylbutanamide

LDA (1.5M soln in cyclohexane; 10.7 mL, 16.04 mmol) was added dropwise to a solution of (6) (2.21 g, 7.64 mmol) in dry THF (20 mL) under nitrogen, and the reaction mixture was stirred at room temperature for 15 min. DMPU (1.94 mL, 16.04 mmol) was added, and the solution was cooled to −82° C. A solution of (5) (2.11 g, 7.64 mmol) in dry THF (5 mL) was added dropwise. The solution was gradually warmed to −40° C. and stirred at this temperature for 4 h and kept at −20° C. overnight. The reaction was quenched with aqueous ammonium chloride and partitioned between ethyl acetate and water. The organic layer was washed with brine, dried, and evaporated to dryness. The crude product was purified by flash column chromatography (hexanes-ethyl acetate, 50:50; v/v) to give (7) (2.18 g, 65%):

NMR (CDCl$_3$) d 0.92 (t, J=7.3 Hz, CH$_3$CH$_2$), 0.95 (d, J=6.5 HZ, CH$_3$CH), 3.54–3.68 (2 m, CH$_2$OH), 4.18–4.25 (m, NCHC), 4.42 (s, PhCH$_2$), 5.30 (2 d, J=2.2 and 7.7, OH), 7.06–7.10 (m, n-PrArH), 7.26–7.35 (m, ArH).

EXAMPLE (8)

2-(3-Benzyloxy-2-(S)-methylpropyl)-4-(R)-(n-Propyl)phenylbutanoic Acid

A solution of (7) (1.87 g, 4.27 mmol) in THF (2 mL) was added 2N HCl (36 mL), and the mixture was heated under reflux with vigorous stirring for 34 h. The reaction was cooled to 0° C., and 2N NaOH (40 mL) was added. After 10 min at 0° C., the solution was acidified with conc HCl to pH 3. The product was extracted with ethyl acetate (3×), and the organic layer was dried and evaporated to a residue, which was purified by flash column chromatography (hexanes-ethyl acetate-acetic acid, 80:20:0.5; v/v) to give (8) (0.984 g, 62%):

NMR (CDCl$_3$) d 0.91 (t, J=7.3 Hz, CH$_3$CH$_2$), 0.92 (d, J=6.6 HZ, CH$_3$CH), 3.21–3.28 (m, BnOCH$_2$), 4.44 (s, PhCH$_2$), 7.06 (s, n-PrArH), 7.31–7.32 (m, ArH); MS m/z 351 (M+1).

EXAMPLE (9)

2-(2-(S)-Benzyloxymethylpropyl)-4-(R)-(n-Propyl)phenylbutanoyl-L-tert-Gly-NHPh EDC (500 mg, 2.61 mmol) was added to a solution of (8) (801 mg, 2.17 mmol), L-tert-Gly-NHPh (449 mg, 2.18 mmol), and 1-hydroxybenzotrizole hydrate (440 mg, 3.26 mmol) in dichloromethane (20 mL), and the mixture was stirred at room temperature overnight. The solution was washed with dil HCl, brine, dried, and evaporated to a residue, which was purified by flash column chromatography (hexanes-ethyl acetate, 85:15 to 80:20; v/v) to give (9) (787 mg, 65%):

NMR (CDCl$_3$) d 0.91 (t, J=7.3 Hz, CH$_3$CH$_2$), 0.94 (d, J=6.6 Hz, CH$_3$CH), 1.08 (s, t-Bu), 3.20–3.30 (m, BnOCH$_2$), 4.45 (s, PhCH$_2$), 4.57 (d, J=9.2 Hz, CHt-Bu), 6.31 (d, J=9.2 Hz, NH), 6.98–7.10, 7.22–7.34 and 7.49 (3 m, ArH), 8.33 (s, NH); MS m/z 464 (M−PhNH).

EXAMPLE (10)

2-(2-(S)-Hydroxymethylpropyl)-4-(R)-(n-Propyl)phenylbutanoyl-L-tert-Gly-NHPh A solution of (9) (565 mg, 1.01 mmol) in methanol (10 mL) was hydrogenated over 20% Pd(OH)$_2$ (113 mg) at 70 psi for 15 h. The catalyst was filtered off and washed with methanol. The combined filtrates were evaporated to a syrup (458 mg):

NMR (CDCl$_3$) d 0.88 (d, J=6.7 Hz, CH$_3$CH), 0.92 (t, J=7.4 Hz, CH$_3$CH$_2$), 1.10 (s, t-Bu), 1.23–1.29 (m, CHCH$_2$OH), 1.60 (q, CH$_3$CH$_2$), 1.75–2.09 (3 m, CH$_2$CH (CO)CH$_2$), 2.45 (m, CHCO), 2.53 and 2.60 (2 t, 2 ARCH$_2$), 2.93, 3.25 and 3.56 (3 m, CH$_2$OH), 4.68 (d, J=9.2 Hz, CHt-Bu), 6.73 (d, J=9.2 Hz, NH), 7.02–7.09, 7.22–7.26 and 7.47–7.49 (3 m, ArH), 8.79 (s, NHPh); MS m/z 467 (M+1).

Anal. calcd. for C$_{29}$H$_{42}$N$_2$O$_3$: C 74.64, H 9.07, N 6.00; found: C 74.37, H 9.14, N 5.84.

EXAMPLE (11)

2-(2-(S)-Carboxypropyl)-4-(R)-(n-Propyl)phenylbutanoyl-L-tert-Gly-NHPh

Jones reagent (2.67M; 0.586 mL, 1.57 mmol) was added dropwise to a stirred solution of (10) (458 mg, 0.98 mmol) in acetone (50 mL) at 0°–5° C. After 0.5 h, 2-propanol was added to destroy excess oxidant. Water (50 mL) was added, and acetone was removed in vacuo. The product was extracted with ethyl acetate (3×). The organic layer was washed with brine, dried, and evaporated to a residue, which was purified by flash column chromatography (hexanes-ethyl acetate-acetic acid, 70:30:0.5; v/v) to give (11) (333 mg, 68% overall yield in two steps):

NMR (CDCl$_3$) d 0.92 (t, CH$_3$CH$_2$), 1.12 (s, t-Bu), 1.13 (d, CH$_3$CH), 1.60 (q, CH$_3$CH$_2$), 2.52 (t, CH$_3$CH$_2$CH$_2$), 4.68 (d, J=8.9 Hz, CHt-Bu), 6.88 (d, J=8.9 Hz, NH), 7.00–7.08 (m ArH), 7.19 (t, ArH), 7.49 (d, ArH), 9.02 (s, NHPh); MS m/z 481 (M+1).

Anal. calcd. for C$_{29}$H$_{40}$N$_2$O$_4$: C 72.47, H 8.39, N 5.83; found: C 72.62, H 8.41, N 5.69.

EXAMPLE (12)

(4S)-3-(1-Oxohexyl)-4-(phenylmethyl)-2-oxazolidone n-Butyllithium (2M soln in pentane; 77 mL, 153.8 mmol) was added dropwise to a stirred solution of (4S)-(phenylmethyl)-2-oxazolidone (25 g, 141.1 mmol) in dry THF (250 mL) at −78° C. under nitrogen. Hexanoyl chloride (21 mL, 149.5 mmol) was added portionwise, and the mixture was kept at −78° C. for 1 h and warmed to 0° C. Saturated aqueous NaHCO$_3$ (100 mL) was added, and the mixture was stirred at 0° C. for 0.5 h. The product was extracted with dichloromethane (3×), and the combined organic extracts were washed with 5% Na$_2$CO$_3$ (100 mL), brine, dried, and evaporated to a syrup. The crude product was purified by flash column chromatography on silica gel (1 kg) with hexanes-ethyl acetate (97:3 to 90:10 to 85:15, v/v) as the eluant. The desired fractions were pooled and evaporated to an oil (36.17 g, 93%):

NMR (CDCl$_3$) d 0.90–0.94 (m, CH$_3$), 1.35–1.39 (m, CH$_3$CH$_2$CH$_2$), 1.68–1.72 (m, CH$_3$CH$_2$CH$_2$CH$_2$), 2.77 (q, J=9.6 and 13.3 Hz, CHCH$_2$O), 3.30 (q, J=3.3 and 13.3 Hz, CHCH$_2$O), 2.93 (m, CH$_2$CO), 4.15–4.23 (m, PhCH$_2$), 4.64–4.70 (m, CHCH$_2$Ph), 7.21–7.36 (m, ArH); MS m/z 276 (M+1).

Anal. calcd. for C$_{16}$H$_{21}$NO$_3$: C 69.79, H 7.69., N 5.09; found: C 69.93, H 7.78, N 5.09.

EXAMPLE (13)

(4S)-3-[1-Oxo-2-(benzyloxymethyl)hexyl]-4-(phenylmethyl)-2-oxazolidone

A solution of (12) (16 g, 58.1 mmol) in dry dichloromethane (110 mL) was cooled to 0° C., degassed, and kept under nitrogen. Titanium(IV) chloride (1M soln in CH$_2$Cl$_2$;

61 mL, 61 mmol) was added portionwise to the vigorously stirred solution producing a bright yellow solution. After 5 min, triethylamine (8.5 mL, 61.3 mmol) was added dropwise giving a deep red homogeneous solution. This enolate solution was stirred at 0° C. for 1 h, after which benzyl chloromethyl ether (~80% pure; 20 mL, 115.5 mmol) was slowly added. The reaction mixture was stirred at this temperature for 3 h and at room temperature for 2 h over which time the dark red color faded to a pale yellow color. The reaction was quenched with saturated ammonium chloride (200 mL). The two layers were separated, and the aqueous layer was back extracted with $CH_2Cl_2$ (2×). The combined organic extracts were washed with aqueous $NaHCO_3$, brine, dried, and evaporated to a yellow oil. The crude product was purified by flash column chromatography (hexanes-ethyl acetate, 90:10; v/v) to give crystalline (13) (20.7 g, 90%):

NMR ($CDCl_3$) d 0.87 (t, J=7.0 Hz, $CH_3CH_2$), 1.23–1.34 (m, $CH_3CH_2CH_2$), 1.52 and 1.70 (2 m, $CH_3CH_2CH_2CH_2$), 2.68 and 3.23 (2 q, $CHCH_2O$), 3.65 and 3.79 (2 q, $BnOCH_2$), 4.12 and 4.17 (2 q, $PhCH_2CH$), 4.24 (m, CHCO), 4.54 (q, $PhCH_2O$), 4.73 (m, $CHCH_2Ph$), 7.18–7.33 (m, ArH); MS m/z 396 (M+1).

Anal. calcd. for $C_{24}H_{29}NO_4$: C 72.89, H 7.39, N 3.54; found: C 72.93, H 7.33, N 3.55.

EXAMPLE (14)

2-(S)-(Benzyloxymethyl)hexanoic Acid

A solution of (13) (12.4 g, 31.35 mmol) in THF (200 mL) and water (50 mL) was cooled to 0° C. Hydrogen peroxide (30 wt %; 12.93 mL, 4 equiv) and lithium hydroxide monohydrate (2.64 g, 62.86 mmol) were added, and the reaction mixture was vigorously stirred at 0° C. for 1 h. A solution of sodium sulfite (17.38 g, 137.94 mmol) in water (69 mL) and a solution of sodium hydrogencarbonate (13.16 g, 156.67 mmol) in water (230 mL) were added successively. The solution was basicified with NaOH to pH 10 and extracted with $CH_2Cl_2$ (3×). The aqueous layer was acidified with HCl, and the product was extracted with ethyl acetate (3×). The organic layer was dried and evaporated to an oil (7.08 g, 96%):

NMR ($CDCl_3$) d 0.89 (t, $CH_3CH_2$), 1.29–1.33 (m, $CH_3CH_2CH_2$), 1.54 and 1.65 (2 m, $CH_3CH_2CH_2CH_2$), 2.72 (m, CHCO), 3.57 and 3.66 (2 q, $BnOCH_2$), 4.55 (s, $PhCH_2$), 7.26–7.35 (m, ArH); MS m/z 237 (M+1).

EXAMPLE (15)

2-(S)-(Benzyloxymethyl)hexanol

Lithium aluminum hydride (1M soln in THF; 30 mL, 30 mmol) was added to a solution of (14) (7.08 g, 29.96 mmol) in dry THF (150 mL), and the mixture was stirred at room temperature for 2 h. Water (1.14 mL), 15% NaOH (1.14 mL), and water (3.42 mL) were added dropwise successively. The solid was was filtered off and washed with THF, and the combined filtrates were evaporated to dryness. The residue was partitioned between dichloromethane and water. The organic layer was separated and washed with brine, dried, and evaporated to give (15) as an oil (6.56 g, 98%):

NMR ($CDCl_3$) d 0.89 (t, J=6.9 Hz, $CH_3CH_2$), 1.20–1.33 [m, $CH_3(CH_2)_3$], 1.88 (m, $CHCH_2O$), 2.63 (q, J=4.4 and 7.0 Hz, OH), 3.46, 3.60–3.67 and 3.70–3.75 (3 m, 2 $CH_2O$), 4.52 (q, $PhCH_2$), 7.27–7.37 (m, ArH); MS m/z 223 (M+1). Compound (15) can also be prepared directly from (14) by reduction with lithium borohydride in THF.

EXAMPLE (16)

2-(S)-(Benzyloxymethyl)hexyl Iodide

N-Iodosuccinimide (10.62 g, 47.2 mmol) was added portionwise to a stirred solution of (15) (6.56 g, 29.5 mmol) and triphenylphosphine (12.38 g, 47.2 mmol) in DMP (100 mL) at 0°–5° C. The brown solution was stirred at room temperature for 2 h. Methanaol and n-butanol were added, and the solution was evaporated to a residue, which was partitioned between ethyl ether and water. The aqueous layer was back extracted with ethyl ether (3×). The combined ethereal layer was washed with sodium bisulfite (2×), brine, dried, and evaporated to a small volume. Triphenylphosphine oxide was filtered off, and the filtrate was evaporated to dryness. The crude product was purified by flash column chromatography (hexanes-ethyl acetate, 98.5:1.5 to 98:2 to 80:20; v/v) to give (16) (7.25 g, 74%):

NMR ($CDCl_3$) d 0.90 (t, $CH_3CH_2$), 1.20–1.37 [m, $CH_3(CH_2)_3$], 3.29–3.35 (m, $CH_2I$), 3.42–3.45 (m, $BnOCH_2$), 4.52 (s, $PhCH_2$), 7.27–7.36(m, ArH).

Anal. calcd. for $C_{14}H_{21}OI$: C 50.61, H 6.37, I 38.20; found: C 50.89, H 6.48, I 38.00.

EXAMPLE (17)

L-Prolinol 4-(4-Fluorophenyl)phenylbutanamide

EDC (10.69 g, 55.75 mmol) was added to a solution of 4-(4-fluorophenyl)phenylbutanoic acid (12g, 46.46 mmol) and L-prolinol (4.56 mL, 46.46 mmol) in dichloromethane (200 mL), and the reaction mixture was stirred at room temperature overnight. The solution was washed with 5N NaOH, dil HCl, brine, dried, and evaporated to a syrup. The crude product was purified by flash column chromatography (hexanes-ethyl acetate, 50:50 to EtOAc; v/v) to give (17) (11.1 g, 70%):

NMR ($CDCl_3$) d 1.52–1.60 and 1.79–1.97 (2 m, $NCCH_2CH_2$), 2.00–2.07 (m, $ArCCH_2C$), 2.34 (t, $CH_2CO$), 2.73 (t, $CH_2Ar$), 3.37–3.49 (m, $NCH_2$), 3.53–3.70 (2 m, $CH_2OH$), 4.19–4.26 (m, NCHC), 5.14 (q, J=2.3 and 7.7 Hz, OH), 7.09–7.54 (3 m, ArH); MS m/z 342 (M+1).

Anal. calcd. for $C_{21}H_{24}FNO_2$: C 73.88, H 7.09, N 4.10, F 5.56; found: C 74.02, H 7.03, N 3.87, F 5.70.

EXAMPLE (18)

L-Prolinol2-[2-(S)-(Benzyloxymethyl)hexyl]-4-(R) - (4-fluorophenyl)phenylbutanamide LDA (1.5M soln in cyclohexane; 20.5 mL, 30.75 mmol) was added dropwise to a solution of (17) (5 g, 14.6 mmol) in dry THF (100 mL) under nitrogen, and the reaction mixture was stirred at room temperature for 15 min. DMPU (3.72 mL, 30.76 mmol) was added, and the solution was cooled to −82° C. A solution of (15) (5.11 g, 15.4 mmol) in dry THF (40 mL) was added dropwise. The solution was gradually warmed to −40° C. and stirred at this temperature for 4 h and kept at −20° C. overnight. The reaction was quenched with aqueous ammonium chloride and partitioned between ethyl acetate and water. The organic layer was washed with brine, dried, and evaporated to dryness. The crude product was purified by flash column chromatography (hexanes-ethyl acetate, 60:40; v/v) to give (18) (4.96 g, 62%):

NMR ($CDCl_3$) d 0.88 (t, $CH_3$), 1.24–1.28 [m, $CH_3(CH_2)_3$], 2.52–2.62 (m, $CH_2Ar$), 2.71–2.78 (m, CHCO), 3.52–3.69 (2 m, $CH_2OH$), 4.21 (m, NCHC), 4.38 (s, $PhCH_2$), 5.34 (q, J=2.1 and 7.8 Hz, OH), 7.10–7.55 (3 m, ArH).

Anal. calcd. for $C_{35}H_{44}FNO_3$: C 77.03, H 8.13, N 2.57, F 3.48; found: C 76.89, H 8.12, N 2.48, F 3.13.

EXAMPLE (19)

2-[2-(S)-(Benzyloxymethyl)hexyl]-4-(R)-(4-fluorophenyl)phenylbutanoic Acid

A solution of (18) (4.74 g, 8.69 mmol) in THF (10 mL) was added 2N HCl (100 mL), and the mixture was heated under reflux with vigorous stirring for 48 h., The solution was cooled to 0° C. and basicified with 5N NaOH. After 10 min at 0° C., the solution was acidified with conc HCl to pH 3. The product and the unreacted starting material were extracted with ethyl acetate (3×), and the organic layer was dried and evaporated to a residue, which was separated by flash column chromatography (hexanes-ethyl acetate-acetic acid, 80:20:0.5; v/v) to give unreacted (18) (0.8 g) and the product (19) (1.9 g, 57% based on the recovered starting material):

NMR (CDCl$_3$) d 0.86 (t, CH$_3$), 1.17–1.29 [m, CH$_3$(CH$_2$)$_3$], 1.33 (m, CCHC), 1.46–2.05 [4 m, CH$_2$CH(CO)CH$_2$)], 2.54–2.75 (m, CHCO and ArCH$_2$), 3.33 (m, BnOCH$_2$), 4.45 (s, PhCH$_2$), 7.08–7.53 (3 m, ArH).

Anal. calcd. for $C_{30}H_{35}FO_3$: C 77.89, H 7.63, F 4.11; found: C 77.61, H 7.47, F 3.91.

EXAMPLE (20)

2-[2-(S)-(Benzyloxymethyl)hexyl]-4-(R)-(4-fluorophenyl) phenylbutanoyl-L-tert-GlyNHMe EDC (50 mg, 0.261 mmol) was added to a solution of (18) (100 mg, 0.216 mmol), L-tert-Gly-NHMe hydrochloride (41 mg, 0.229 mmol), N-methylmorpholine (29 mL, 0.264 mmol), and 1-hydroxybenzotrizole hydrate (44 mg, 0.326 mmol) in DMF (3 mL), and the mixture was stirred at room temperature overnight. Ethyl ether and water were added, and the aqueous layer was back extracted with ethyl ether (2×). The combined ethereal extracts were washed with brine, dried, and evaporated to dryness. The crude product was purified by preparative TLC (hexanes-ethyl acetate, 60:40; v/v) to give (20) (94 mg, 74%):

NMR (CDCl$_3$) d 0.86 (t, CH$_3$), 0.99 (s, t-Bu), 2.79 (d, J=4.8 Hz, NCH$_3$), 3.31 (q, BnOCH$_2$), 4.24 (d, J=9.2 Hz, NHCHCO), 4.45 (s, PhCH$_2$), 5.92 (br s, NHCH$_3$), 6.19 (d, NHCH), 7.08–7.52 (3 m, ArH).

EXAMPLE (21)

2-[2-(S)-(Hydroxymethyl)hexyl]-4-(R)-(4-fluorophenyl)phenylbutanoyl-L-tert-GlyNHMe A solution of (20) (88 mg, 0.149 mmol) in methanol (3 mL) was hydrogenated over 20% Pd(OH)$_2$ (21 mg) at 40 psi for 6 h. The catalyst was filtered off and washed with methanol. The combined filtrates were evaporated to a residue, which was purified by preparative TLC (hexanes-ethyl acetate, 60:40; v/v) to give (21) (61 mg, 82%): MS m/z 499 (M+1).

EXAMPLE (22)

2-[2-(S)-(Carboxy)hexyl]-4-(R)-(4-fluorophenyl) phenylbutanoyl-L-tert-GlyNHMe

Jones reagent (2.67M; 66.6 mL, 0.176 mmol) was added to a stirred solution of (21) (54.4 mg, 0.109 mmol) in acetone (5 mL) at 0°–5° C. After 0.5 h, 2-propanol was added to destroy excess oxidant. Water was added, and acetone was removed in vacuo. The product was extracted with ethyl acetate (3×). The organic layer was washed with brine, dried, and evaporated to a residue, which was purified by flash column chromatography (hexanes-ethyl acetate-acetic acid, 60:40:0.5; v/v) to give (22) (46.5 mg, 83%):

NMR (CDCl$_3$) d 0.88 (t, CH$_3$), 1.04 (s, t-Bu), 1.25–1.30 [m, CH$_3$(CH$_2$)$_3$], 2.78 (d, J=4.7 Hz, NCH$_3$), 4.48 (d, J=9.5 Hz, NHCHCO), 6.75 (br s, NHCH$_3$), 7.01–7.42 (3 m, ArH) 7.79 (d, NHCH); MS m/z 513 (M+1).

What is claimed is:

1. A process for making a compound of structural formula I:

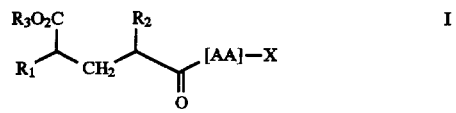

or a pharmaceutically acceptable salt thereof wherein:

$R_1$ is hydrogen, substituted $C_{1-8}$alkyl, or substituted $C_{2-8}$alkenyl wherein the substituent is selected from the group consisting of:

(a) hydrogen, (b) carboxy, (c) Aryl wherein the Aryl group is selected from the group consisting of (1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzothiazolyl, and
(27) benzoxazolyl, and mono and di-substituted Aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(d)

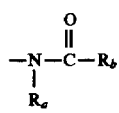

wherein $R_a$ and $R_b$ are each independently hydrogen; Aryl and mono and di-substituted Aryl as defined above (c); or substituted $C_{1-6}$alkyl wherein the substitutent is selected from hydroxy, halo, and phenyl, or wherein $R_a$ and $R_b$ are joined such that together with the nitrogen and carbon atoms to which they are attached, there is formed a saturated or unsaturated lactam,

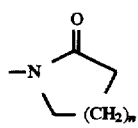

wherein n is 1, 2 or 3 or benzo fused lactam ring,

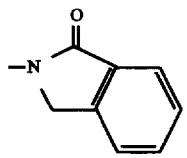

wherein the lactam portion thereof is a ring of 5, 6, 7 or 8 carbon atoms, said lactam or benzolactam to have a single heteroatom belonging to the group consisting of O, N or S;

(e)

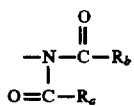

wherein $R_a$ and $R_b$ are each independently hydrogen; Aryl and mono and di-substituted Aryl as defined above (c); or substituted $C_{1-6}$alkyl wherein the substitutent is selected from hydroxy, halo, and phenyl, or wherein $R_a$ and $R_b$ are joined such that together with the nitrogen and carbon atoms to which they are attached, there is formed a saturated or unsaturated lactim (or imide),

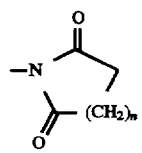

wherein n is 1, 2 or 3 or benzolactim or imide ring such,

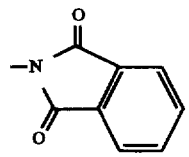

wherein the lactim portion thereof is a ring of 5, 6, 7 or 8 carbon atoms, said lactim or benzolactim to have a single heteroatom belonging to the group consisting of O, N, or S;

(f) amino and mono or disubstituted amino wherein the substituent is selected from $C_{1-6}$ alkyl and Aryl where aryl is defined in (c);

(g)

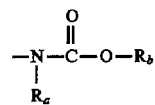

Wherein $R_a$ and $R_b$ are each independently hydrogen; or $C_{1-6}$ Alkyl; or ArylC$_{0-6}$Alkyl or mono or di substituted ArylC$_{0-6}$Alkyl wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen and oxygen atoms to which they are attached, them is formed a saturated or unsaturated monocyclic urethane or fused benzo cyclic urethane,

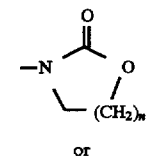

or

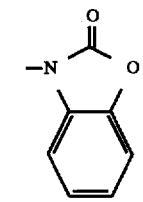

wherein the urethane ring contains 4, 5, 6 or 7 carbon atoms, said ring to contain 2 heteroatoms belonging to the group consisting of N, O or S;

(h)

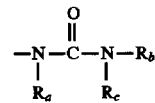

Wherein $R_a$, $R_b$, and $R_c$ are each independently hydrogen; or $C_{1-6}$ Alkyl; or ArylC$_{0-6}$Alkyl or mono or di substituted ArylC$_{0-6}$Alkyl wherein the substitutents are independently selected from $C_{1-6}$alkyl, $C_{1-6}$alkyloxy, halo, hydroxy, amine, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen atoms to which they are attached, there is formed a saturated or unsaturated monocyclic urea or fused benzo cyclic urea,

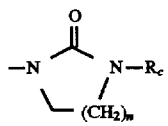

-continued or

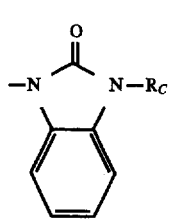

wherein the urea ring contains up to 8 atoms, said ring to contain 2 heteroatoms belonging to the group consisting of O, N, or S; or $R_b$ and $R_c$ are joined such that together with the nitrogen atom to which they are attached, there is formed a saturated or unsaturated monocyclic ring or fused benzo ring containing 5, 6, 7 or 8 atoms, said ring to contain 1 heteroatom belonging to the group consisting of O, N, or S;

(i)

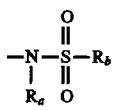

Wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substituents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen and sulfer atoms to which they are attached, there is formed a saturated or unsaturated monocyclic sulfonaminde or benzofused cyclic sulfonamide,

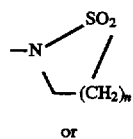

or

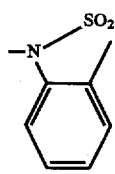

wherein the sulfonamide ring contains 5, 6, 7 or 8 carbon atoms, said ring to contain 2 heteroatoms belonging to the group consisting of N, O, S(O)$_p$ wherein p is an integer from 0–2;

(j)

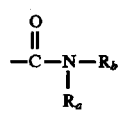

Wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or $R_a$ and $R_b$ are joined such that together with the nitrogen atom to which they are attached, there is formed a saturated or unsaturated monocyclic ring or benzofused ring containing 5, 6, 7 or 8 atoms, said ring to contain 1 heteroatom;

(k)

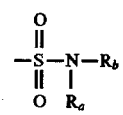

Wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substituents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or $R_a$ and $R_b$ are joined such that together with the nitrogen atom to which they are attached, there is formed a saturated or unsaturated monocyclic ring or benzofused ring containing up to 8 atoms, said ring to contain 1 heteroatom;

$R_2$ is $C_{1-12}$ alkyl, aryl$C_{1-4}$alkyl, aryl substituted $C_{1-4}$alkyl, (aryl$C_{1-4}$alkyl)aryl$C_{1-4}$alkyl, or biaryl$C_{1-4}$alkyl wherein the substituent is $C_{1-3}$alkyl or hydroxy, and wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl,
and mono and di-substituted Aryl as defined above in items (1) to (27) wherein the substitutents on the aryl group are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

R₃ is
(a) H,
(b) Z, where Z is a pharmaceutically acceptable counterion,
(c) $C_{1-10}$alkyl,
(d) Aryl or Aryl $C_{1-3}$alkyl, wherein the aryl group is selected from the group consisting of
  (1) phenyl, and
  (2) substituted phenyl, wherein the substitutent is carboxy, carboxy$C_{1-3}$alkyl, aminocarbonyl, $C_{1-6}$alkylaminocarbonyl;

AA is a single bond or an amino acid of formula II

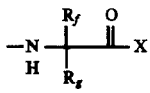

wherein $R_f$ and $R_s$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$alkyl, or $C_{1-4}$alkyloxy,
(k) substituted indolyl $C_{1-6}$alkyl, wherein the substitutent is hydrogen, hydroxy, carboxy, $C_{1-4}$alkyl, or $C_{1-4}$alkyloxy,
(l) substituted imidazolyl $C_{2-6}$alkyl wherein the substitutent is hydrogen, hydroxy, carboxy, $C_{1-4}$alkyl, or $C_{1-4}$alkyloxy,
(m) substituted pyridyl $C_{1-6}$alkyl wherein the substitutent is hydrogen, hydroxy, carboxy, $C_{1-4}$alkyl, or $C_{1-4}$alkyloxy,
(n) substituted pyridyl amino $C_{1-6}$alkyl wherein the substitutent is hydrogen, hydroxy, carboxy, $C_{1-4}$alkyl, or $C_{1-4}$alkyloxy,
(o) substituted pyrimidinyl $C_{1-6}$alkyl wherein the substitutent is hydrogen, hydroxy, carboxy, $C_{1-4}$alkyl, or $C_{1-4}$alkyloxy, X is

wherein $R_5$ and $R_6$ are each individually selected from the group consisting of:
(a) H,
(b) $C_{1-10}$alkyl,
(c) Aryl or Aryl$C_{1-6}$alkyl, wherein the aryl group is selected from the group consisting of
  (1) phenyl,
  (2) naphthyl,
  (3) pyridyl,
  (4) pyrryl,
  (5) furyl,
  (6) thienyl,
  (7) isothiazolyl,
  (8) imidazolyl,
  (9) benzimidazolyl,
  (10) tetrazolyl,
  (11) pyrazinyl,
  (12) pyrimidyl,
  (13) quinolyl,
  (14) isoquinolyl,
  (15) benzofuryl,
  (16) isobenzofuryl,
  (17) benzothienyl,
  (18) pyrazolyl,
  (19) indolyl,
  (20) isoindolyl,
  (21) purinyl,
  (22) carbazolyl,
  (23) isoxazolyl,
  (24) benzthiazolyl,
  (25) benzoxazolyl,
  (26) thiazolyl, and
  (27) oxazolyl, and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl; comprising adding a compound of formula 9

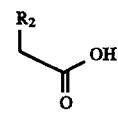

wherein $R_2$ is described as above, and L-prolinol to a solvent, selected from the group consisting of dichloromethane, benzene, toluene, cyclohexane, heptane and carboiimide while maintaining a temperature of about 20° C. to about 30° C. to produce a solution containing a compound of structural formula 10

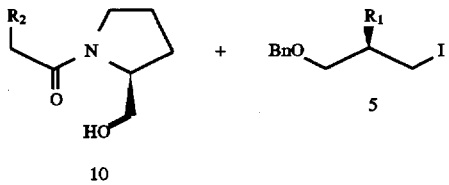

wherein $R_2$ is described above, adding to the solution a strong base in an ether in the presence of DMPU, cooling the solution to from about −100° C. to −50° C., adding a solution of a protected alkyl halide 5, wherein $R_1$ is described above, and warming the solution to from about −40° C. to about −20° C. to produce a solution containing a compound of structural formula 11

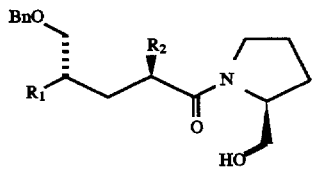

wherein $R_1$ and $R_2$ and R' are described above, adding to a solution containing a compound of structural formula 11 in THF-H2O a mineral acid, and heating the solution to from about 50° C. to about 100° C. to produce a solution containing a compound of structural formula 12

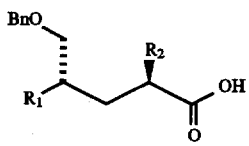

(12)

wherein $R_1$ and $R_2$ and R' are described above, coupling the compound of structural formula 12 with an amino acid, followed by hydrolysis to produce a compound of structural formula 13

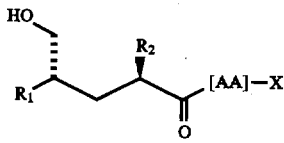

(13)

wherein $R_1$ and $R_2$ and R', AA, and X are described above, oxidizing a compound of structural formula 13 at a temperature of about −10° C. to about 2° C. using a Jones reagent to produce a compound of structural formula 14

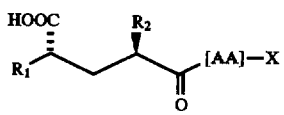

(14)

wherein R1, R2 AA, and X are described above and isolating the compound of structural formula 14.

2. A process according to claim 1 wherein: $R_1$ is substituted $C_{1-8}$alkyl.

3. A process according to claim 1 wherein: the solvent is EDC.

4. A process according to claim 1 wherein: the strong base is LDA, $LiN(SiMe_3)_2$ or $KN(SiMe_3)_2$.

5. A process according to claim 1 wherein the ether is tetrahydrofuran, ethyl ether, or methyl propyl ether.

6. A process according to claim 1 wherein: the mineral acid is HCl or H2SO4.

7. A process according to claim 5 wherein: the mount of mineral acid is from about 2 to about 10N.

8. A process according to claim 4 wherein the strong acid is LDA.

9. A process according to claim 5 wherein the ether is tetrahydrofuran.

10. A process for making a compound of structural formula I:

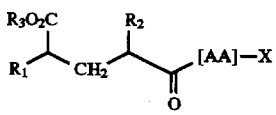

(I)

or a pharmaceutically acceptable salt thereof wherein:
$R_1$ is substituted $C_{1-8}$ alkyl
$R_2$ is $C_{1-12}$ alkyl, $arylC_{1-4}alkyl$, aryl substituted $C_{1-4}alkyl$, $(arylC_{1-4}alkyl)$-$arylC_{1-4}alkyl$, or $biarylC_{1-4}alkyl$ wherein the substituent is $C_{1-3}alkyl$ or hydroxy, and wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents on the aryl group are independently selected from $C_{1-6}alkyl$, $C_{1-6}alkyloxy$, $hydroxyC_{1-6}alkyl$, $C_{1-6}alkoxyC_{1-6}alkyl$, halo, hydroxy, amino, $C_{1-6}alkylamino$, $aminoC_{1-6}alkyl$, carboxyl, $carboxylC_{1-6}alkyl$, and $C_{1-6}alkylcarbonyl$;

$R_3$ is
(a) H,
(b) Z, where Z is a pharmaceutically acceptable counterion,
(c) $C_{1-10}alkyl$,
(d) Aryl or Aryl $C_{1-3}$ alkyl, wherein the aryl group is selected from the group consisting of
(1) phenyl, and
(2) substituted phenyl, wherein the substitutent is carboxy, $carboxyC_{1-3}alkyl$, aminocarbonyl, $C_{1-6}alkylaminocarbonyl$;

AA is a single bond or an amino acid of formula II

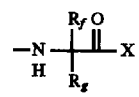

(II)

wherein $R_f$ and $R_g$ are individually selected from:
(a) hydrogen,
(b) $C_{1-6}alkyl$,
(c) mercapto $C_{1-6}alkyl$,
(d) hydroxy $C_{1-6}alkyl$,
(e) carboxy $C_{1-6}alkyl$,
(f) amino substituted $C_{2-6}alkyl$
(g) aminocarbonyl $C_{1-6}alkyl$,
(h) mono- or di-$C_{1-6}alkyl$ amino $C_{2-6}alkyl$,
(i) guanidino $C_{2-6}alkyl$,
(j) substituted phenyl $C_{1-6}alkyl$, wherein the substitutent is hydrogen, hydroxy, carboxy, $C_{1-4}$ alkyl, or $C_{1-4}alkyloxy$,
(k) substituted indolyl $C_{1-6}alkyl$, wherein the substitutent is hydrogen, hydroxy, carboxy, $C_{1-4}$ alkyl, or $C_{1-4}alkyloxy$,
(l) substituted imidazolyl $C_{2-6}alkyl$ wherein the substitutent is hydrogen, hydroxy, carboxy, $C_{1-4}$ alkyl, or $C_{1-4}alkyloxy$,
(m) substituted pyridyl $C_{1-6}alkyl$ wherein the substitutent is hydrogen, hydroxy, carboxy, $C_{1-4}$ alkyl, or $C_{1-4}alkyloxy$,
(n) substituted pyridylamino $C_{1-6}alkyl$ wherein the substitutent is hydrogen, hydroxy, carboxy, $C_{1-4}$ alkyl, or $C_{1-4}alkyloxy$, (o) substituted pyrimidinyl $C_{1-6}$alkyl wherein the substitutent is hydrogen, hydroxy, carboxy, $C_{1-4}$ alkyl, or $C_{1-4}$alkyloxy, X is

wherein $R_5$ and $R_6$ are each individually selected from the group consisting of:
(a) H,
(b) $C_{1-10}$alkyl,
(c) Aryl or Aryl$C_{1-6}$alkyl, wherein the aryl group is selected from the group consisting of
 (1) phenyl,
 (2) naphthyl,
 (3) pyridyl,
 (4) pyrryl,
 (5) furyl,
 (6) thienyl,
 (7) isothiazolyl,
 (8) imidazolyl,
 (9) benzimidazolyl,
 (10) tetrazolyl,
 (11) pyrazinyl,
 (12) pyrimidyl,
 (13) quinolyl,
 (14) isoquinolyl,
 (15) benzofuryl,
 (16) isobenzofuryl,
 (17) benzothienyl,
 (18) pyrazolyl,
 (19) indolyl,
 (20) isoindolyl,
 (21) purinyl,
 (22) carbazolyl,
 (23) isoxazolyl,
 (24) benzthiazolyl,
 (25) benzoxazolyl,
 (26) thiazolyl, and
 (27) oxazolyl
and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl; comprising adding a compound of formula 9

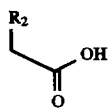

wherein $R_2$ is described as above, and L-prolinol to a solvent belonging to a group consisting of dichloromethane, benzene, toluene, cyclohexane, heptane, and carbodiimides, while maintaining a temperature of about 20° C. to about 30° C. to produce a solution containing a compound of structural formula 10

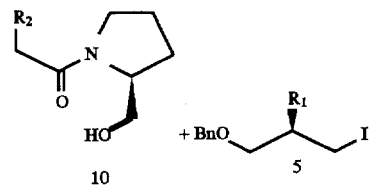

wherein $R_2$ is described above, adding to the solution LDA in tetrahydrofuran in the presence of DMPU, cooling the solution to from about −100° C. to −50° C., adding a solution of a protected alkyl halide 5, wherein $R_1$ is described above, and warming the solution to from about −40° C. to about −20° C. to produce a solution containing a compound of structural formula 11

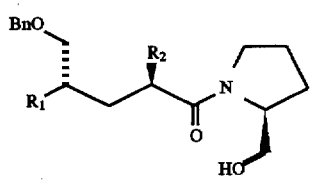

wherein R1, $R_2$ and R' are described above, adding to a solution containing a compound of structural formula 11 in THF-H2O from about 2N to about 10N of a mineral acid belonging to the group consisting of HCl, or $H_2SO_4$ and heating the solution to from about 50° C. to about 100° C. to produce a solution containing a compound of structural formula 12

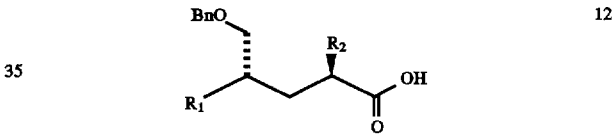

wherein $R_1$, $R_2$ and R' are described above, coupling the compound of structural formula 12 with an amino acid, followed by hydrolysis to produce a compound of structural formula 13

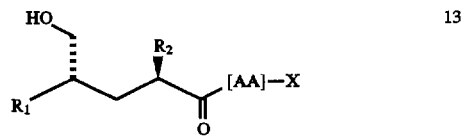

wherein $R_1$, $R_2$, R', AA, and X are described above, oxidizing a compound of structural formula 13 at a temperature of about −10° C. to about 2° C. using a Jones reagent to produce a compound of structural formula 14

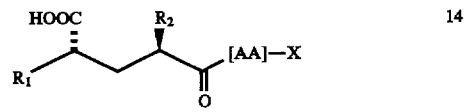

wherein R1, R2 AA, and X are described above and isolating the compound of structural formula 14.

* * * * *